United States Patent
Klemm et al.

[11] Patent Number: 5,958,465
[45] Date of Patent: Sep. 28, 1999

[54] APPARATUS FOR THE PRODUCTION OF DRUG-CONTAINING IMPLANTS IN THE FORM OF STRINGS OF BEADS

[75] Inventors: Klaus Klemm, Frankfurt; Ben Bilberger, Giessen, both of Germany

[73] Assignee: Merck Patent Gesellschaft, Darmstadt, Germany

[21] Appl. No.: 08/804,926

[22] Filed: Feb. 24, 1997

[30] Foreign Application Priority Data

Feb. 22, 1996 [DE] Germany ............ 196 06 490

[51] Int. Cl.⁶ .................................. B29C 45/16
[52] U.S. Cl. ............. 425/116; 425/127; 425/129.1
[58] Field of Search ................... 425/116, 122, 425/127, 129.1

[56] References Cited

U.S. PATENT DOCUMENTS

| | | | |
|---|---|---|---|
| 4,793,785 | 12/1988 | Osada | 425/542 |
| 4,806,405 | 2/1989 | Liebl | 425/122 |
| 5,464,339 | 11/1995 | Arakawa et al. | 425/542 |

FOREIGN PATENT DOCUMENTS

| | | |
|---|---|---|
| 0 157 909 | 10/1985 | European Pat. Off. . |
| 0 157 910 | 10/1985 | European Pat. Off. . |
| 2 320 273 | 11/1974 | Germany . |
| 26 51 441 | 5/1978 | Germany . |

*Primary Examiner*—Tim Heitbrink
*Attorney, Agent, or Firm*—Millen, White, Zelano & Branigan

[57] ABSTRACT

An apparatus for the production of drug-containing implants in the form of strings of beads, comprising chains of small drug-containing plastic bodies respectively arranged in series on a surgical wire or thread, has two elongate mold halves (1), which are accommodated in a mold housing (2). In the mutually facing mold parting surfaces (3) of the two mold halves (1) there are made two rows of mold cavities (4) for receiving in each case a small plastic body and a surgical wire or thread (6) joining the said bodies. The mold cavities (4) are respectively connected to a gate (14) opening out at, a mold outer surface (12 or 13). In each case, a plurality of mold cavities (4) of a row are connected to a common runner (15) which is made in an inner wan of the mold housing and into which there respectively opens out an injection opening (16) adapted such that it can be connected in a sealed manner to an injection device (1).

7 Claims, 3 Drawing Sheets

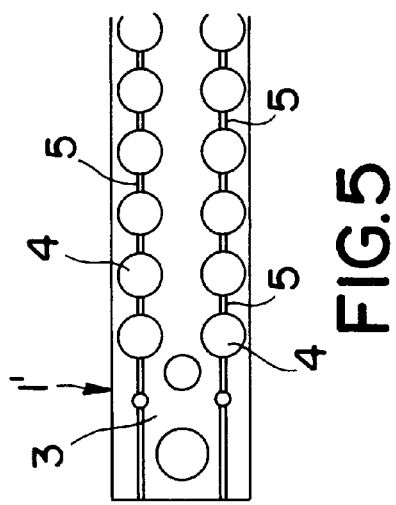
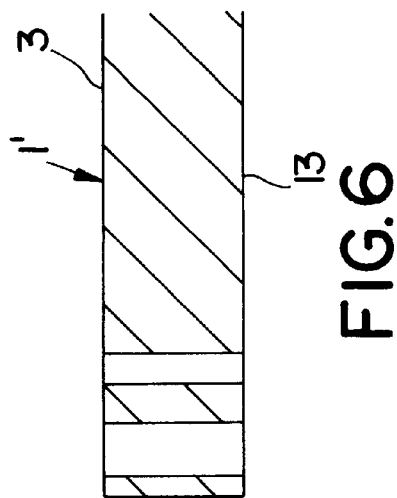
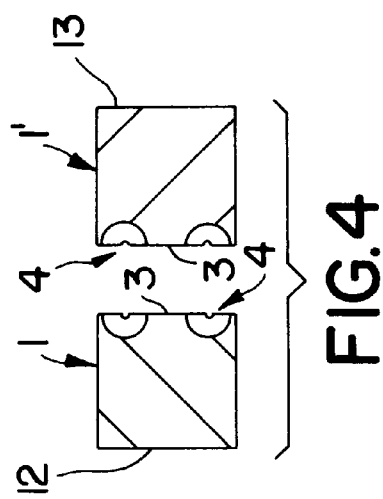
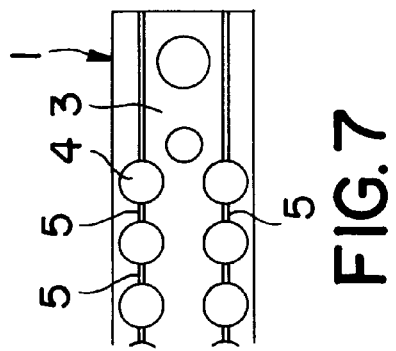
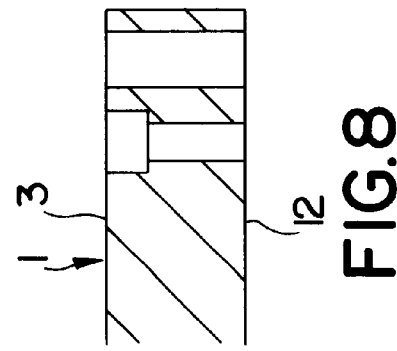

APPARATUS FOR THE PRODUCTION OF DRUG-CONTAINING IMPLANTS IN THE FORM OF STRINGS OF BEADS

FIELD OF THE INVENTION

The invention relates to an apparatus for the production of drug-containing implants in the form of strings of beads, comprising chains of small drug-containing molded bodies respectively arranged in series on a surgical wire or thread.

BACKGROUND OF THE INVENTION

In the care of wounds inflicted in an operation or by injury and at risk of infection, plastic implants which contain antibiotic drugs and release them continuously over a specific period of time are often used. For certain indications, small drug-containing plastic bodies drawn onto surgical wires or threads in the manner of a string of beads have proven successful (German Patent 23, 20 373, German Patent 26 51 441, European Patent 0 157 909, European Patent 0 157 910, incorporated herein by reference).

An advantage of these chains of small drug-containing bodies in comparison with other implants for the local release of active substance is that the surgeon can make an adjustment according to the size of the site of the wound and the requirement for active substance by simply cutting the chains to length. A further advantage is that, after the end of therapy or once the chains are depleted, they can be removed in one piece from the body area in a comparatively simple operation. Generally serving as the polymer matrix for the small drug-containing bodies are polymer materials based on poly(meth)acrylates.

The industrial production of such chains of small drug-containing plastic bodies takes place by extruding a mixture of powdered or granulated poly(meth)acrylate polymer and the pharmaceutical active substance as well as further additives, if appropriate, and molding it by the injection-molding process in a mold to form, for example, small spherical bodies, these being intermittently injection-molded onto a thread or wire passed through the mold.

For production technology reasons, commercial reasons and, not least, licensing reasons, industrially produced implants in the form of strings of beads cannot be offered with just any desired pharmaceutical active substances or in just any desired amounts. However, over and above the ready-made products charged with a predetermined amount of active substance, surgeons often have a need to carry out therapy with implants of this type which allow an individual selection, combination or adjustment of active substance. This can be accomplished by producing such implants themselves before or during the operation, in which case the active substance is formulated according to case-specific specifications.

The use of bone cement based on poly(meth)acrylate polymer as a matrix material for drug-containing implants is known. Bone cements are self-setting mixtures which generally comprise essentially a powdered solid component of poly(meth)acrylate and a liquid component of a (meth) acrylate. By mixing these components, it is possible to obtain compositions of low to high viscosity which, due to the presence of polymerization initiators, cure within a period of time of typically about 10–20 minutes. Such mixtures, mixed with pharmaceutical active substances, may likewise serve for producing drug-containing implants, the not yet cured composition being injected into corresponding molds. This production variant is suitable for manual production, in particular the processing time of the bone cement mixture is only short.

SUMMARY OF THE INVENTION

The object of the invention is to provide an apparatus for, the production of drug-containing implants in the form of strings of beads which make it possible to produce these implants manually with individual charging with active substance even before or during an operation.

This object is achieved according to invention by (i) two elongate mold halves (1), accommodated in a mold housing (2), being adapted by a positioning means (18) and being pressed against each other with their mold parting surfaces (3) by a pressure-exerting means (7), in order to make them seal tight, by (ii) there being made in the mutually facing mould parting surfaces (3) mould cavities (4), arranged at least in one row, for receiving in each case a small moulded body and a wire or thread (6) joining the said bodies, by (iii) the mould cavities (4) being respectively connected to a gate (14) opening out at a mould outer surface (12 or 13), and by (iv) in each case a plurality of mould cavities (4) of a row being connected to a common runner (15) which is made in an inner wall of the mould Lousing and into which there respectively opens out an injection opening (16) adapted such that it can be connected in a sealed manner to an injection device (1).

The simple structural design of the apparatus makes it possible to produce the implants, the bone cement used as matrix material being mixed with the pharmaceutical active substance of the respectively required type, quantity and composition only immediately before production. Since the two mould halves are enclosed and held by the mould housing, of a simple structural design, the entire apparatus is of a simple structural design and can therefore be handled in am easy way. The entire procedure can be performed by one person, without any special tools or additional devices being required for the purpose.

By virtue of its simple structural design, the apparatus is easy to clean, so that use as often as desired, even in quick succession, is made possible. Since each injection opening is connected to a plurality of mould cavities, a plurality of small moulded bodies arranged in series on the wire or thread can be produced in a single injection procedure.

The gates are at the same time placed in such a way that there is least possible distance between the mould cavities (4) and the mould parting surfaces (12, 13).

According to a preferred embodiment of the invention, it is provided that in the two mould halves there are made two parallel rows of mould cavities, the gates of which open out in opposing mould outer surfaces, and that the runners and the injection openings are arranged in mutually opposing walls of the mould housing. This achieves the effect that injection is performed from two sides and in this way two chains of implants can be produced in a single injection-moulding procedure.

The pressure-exerting means (7) according to the invention is to be understood as meaning all devices which serve the purpose of pressing the mould halves (1) so firmly against each other that the flowable material introduced into the mould under pressure via the injection openings (6) cannot escape elsewhere. Primarily suitable for this purpose are clips and, in particular, screw connections. The pressure-exerting means may both include the mould housing (2) and, as preferred, grasp firmly around the mould half parts alone. Countersunk screw connections of the mould half parts, perpendicular with respect to their mould parting surfaces (3), are preferred.

The positioning means (18) according to the invention are to be understood to mean all devices which serve the purpose of fixing the mould halves (1) exactly and quickly in their position in relation to one another, so that an optimum mould is produced. Suitable for this are pins, bolts, studs, grooves etc., which must have a corresponding counterpart in the form of a depression on the opposing mould half. Bolts and bolt holes are suitable with preference for positioning.

Further advantageous refinements of the inventive idea are the subject of further subclaims.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein:

FIG. 4 shows an enlarged partial section through the two separated mould halves in a region of the screw-like pressure-exerting means;

FIG. 5 is a front face view of one mold half;

FIG. 6 is a side elevation of the mold half of FIG. 5;

FIG. 7 is a front face view of The other mold half;

FIG. 8 is a side elevation of the mold half of FIG. 7;

DETAILED DESCRIPTION

Figure 1:
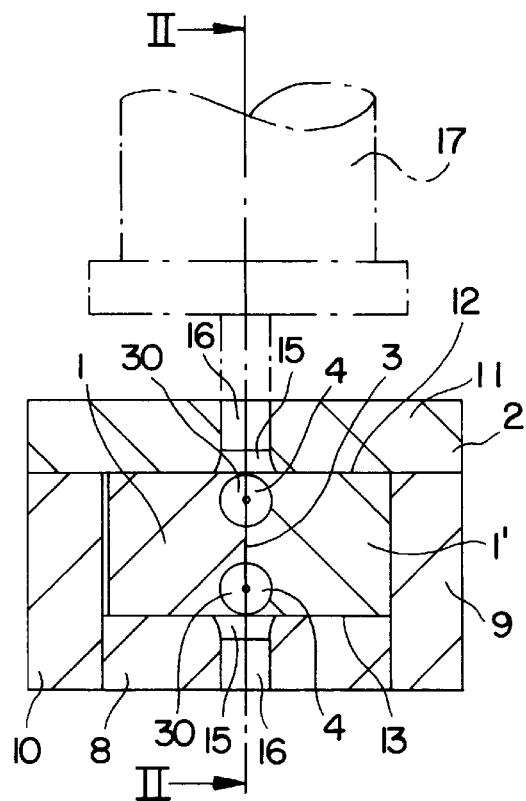
FIG. 1 shows a cross-section through an apparatus for the production of drug-containing implants in the form of strings of beads.
Figure 3:
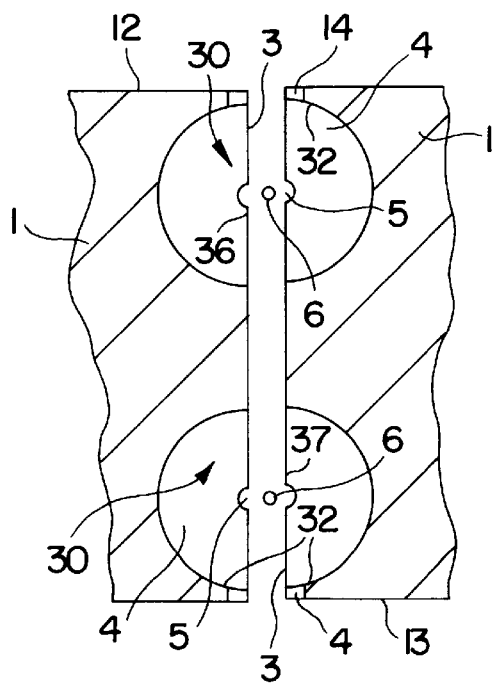
FIG. 3 shows an enlarged partial section through the two mold halves in the region of their mold parting surfaces.

The apparatus represented id the drawing serves the purpose of producing from a mixture of bone cement and pharmacological active substances a drug-containing implant in the form of a string of beads which comprises a chain of small plastic bodies which are arranged in series on a surgical wire or thread. As can be seen-from FIG. 1, two elongate mould halves (11), which are accommodated in a mould housing (2), enclose in their mutually facing mould parting surfaces (3) two rows of mould cavities (4), which in the case of the exemplary embodiment represented are spherically shaped. Each mould cavity half in each mould half (1) is therefore hemispherical. Neighbouring mould cavities (4) of each row are connected by short channels (5), into which a surgical thread (6) or wire is laid, before closing the mould, as a carrier core for the implant to be produced.

The two mould halves (1) are pressed against each other with their mould parting surfaces (3) by a pressure-exerting means. This pressure-exerting means comprises, for example, a plurality of pressure-exerting screws (7), which are provided in the mould halves perpendicularly with respect to the mould parting surfaces (3).

A housing base (8) and two side walls (9) and (10), screwed on laterally thereto, form a crosssectionally U-shaped basic housing part, which is closed by a removably fastened housing cover (11).

The mould cavities (4) are connected in each case to a gate (14), opening out at the upper mould outer surface (12) or the lower mould outer surface (13), respectively. These gates (14) lie in the region of the mould parting surface (3) and at the points at which the spherical mould cavities (4) in each case have the least possible distance from the respectively neighbouring mould outer surface (12) or (13). As a result, the gates (14) are minimized, so that, when the finished implant is released, there remains virtually no troublesome sprue.

Figure 2:
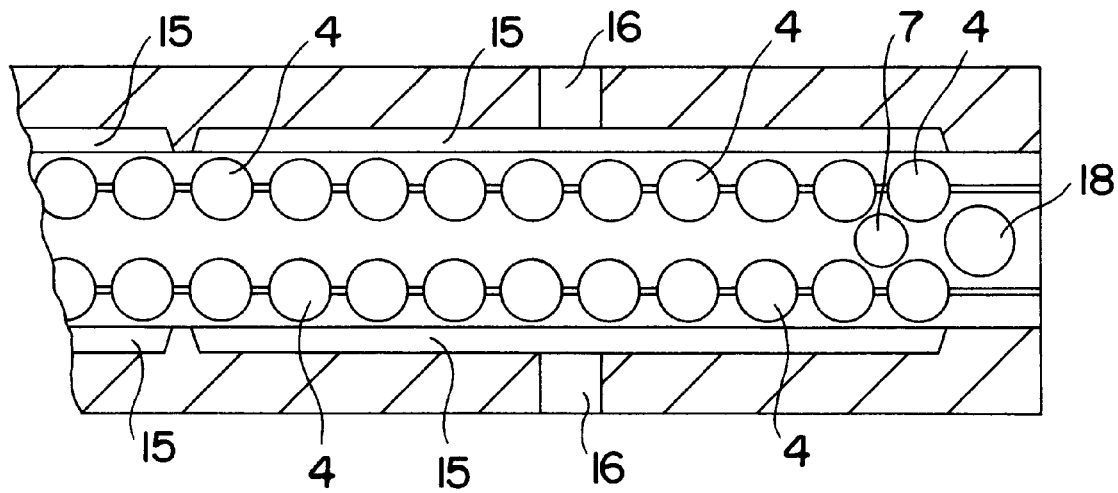
FIG. 2 shows a section along the line II—II in FIG. 1.

As can be seen from FIG. 2, in each case a plurality of mould cavities (4) of a row are connected to a common runner (15) which is made in an inner wall of the housing cover (1) or of the housing base (8). Into each runner (15) there opens out an injection opening (16), which leads to the outside of the housing and, for carrying out the injection-moulding procedure, can be connected in a sealed manner to an injection device, for example a filling syringe (17), only partially indicated by dot-dashed lines in FIG. 1. For each row of mould cavities (4) there are provided a plurality of mutually aligned runners (15), into which there opens out in each case a separate injection opening (16).

After laying in the surgical thread (6) or wire, the two mould halves (1) are brought into the correct position by the positioning means (18), pressed against each other by the pressure-exerting means (7), in order to make them sealtight and to close the mould, and are introduced into the housing (2) Then, all or the respectively desired number of mould cavities (4) are filled with the flowable mixture of bone cement and active substance by means of the filling syringe (17), connected to the injection openings (6) one after the other. After the bone cement has cured, first of all the cover screw connection of the mould housing is released, an abrupt force (for example a hammer blow) is exerted on the mould halves, in order to shear the mould halves off the sprue, and the two could halves (1) are taken out. After releasing the pressure-exerting means (7), the mould halves are separated and the moulded implant chains are removed. The sprue remaining in the runners (15) and in the injection openings (16) may be removed in an easy way, so that the apparatus can be reassembled immediately thereafter and used for a further moulding procedure.

The entire disclosures of all applications, patents and publications, cited above and below, and of corresponding application German 19606490.2, filed Feb. 22, 1996, are hereby incorporated by reference.

In summary, an apparatus for moulding implants containing pharmaceutically active substances within a hardenable material which is configured as a string of beads includes the first and second mold halves 1 and 1', each having at least one row of semi-spherical recesses 4 therein, which when opposed, form spherical chambers 30 (see FIG. 1). Each spherical chamber has an outer wall portion 32 adjacent to outer wall, 12 and 13 of the mold halves 1 and 1' and interior wall portions 36 and 37 disposed generally normal to the outer wall portions. The gates 14 form first passages through the outer walls 34 of the mold halves 1 and 1' to the spherical chambers 30. The second passages 5 which extend through the interior wall portions 36 and 37 of the spherical chambers 30 and extend in the mold halves 1 and 1' connecting adjacent spherical chambers in series.

As is seen in FIG. 1, the first and second mold halves 1 and 1' are held together by the side walls 9 and 10 with the semi-spherical recesses 4 aligned so as to form the spherical chambers 30. The removably fastened housing cover 11 forms a body which is disposed outside of the outer walls 12 and 13 of the mold halves 1 and 1' while the runners 15 form spaces in communication with the first passages formed by the gates 14. By utilizing this arrangement, a strand is placed in the second passages and passes through the spheres 30 and a mixture of hardenable material, such as bone cement 30, which has a pharmaceutically active substance therein, is injected into a space defined by a runner 15, the hardenable material flows into the spherical chambers and bonds with the strand to form a string of treatment beads. When there are two rows of spherical chambers 30 and two runners 15 forming spaces on opposite sides of the joined mold halves, two strings of treatment beads are produced.

Figure 9:
FIG. 9 is a side view of a strand according to the prior art which may be a wire or thread which is used in making strings of treatment beads according to the present invention.
Figure 10:
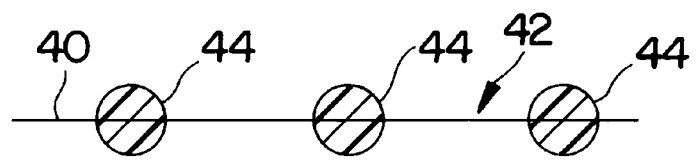
FIG. 10 is a side view of a string of treatment beads according to the prior art with the beads in cross-section and formed on the strand of FIG. 9.

As seen in FIGS. 9 and 10, a strand 40 which may be a wire or thread is used to form a string of treatment beads 42 having beads 44 formed of hardened bone cement incorporating therein a pharmaceutically active substance.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An arrangement for the on site production of drug-containing implants in the form of at least one string of beads, comprising chains of small drug-containing molded bodies arranged in series on a surgical wire or thread, the arrangement comprising in combination:

bone cement;

at least one pharmaceutically active substance for mixing with the bone cement;

a length of wire or thread;

a mold housing;

two elongate mold halves for positioning in the mold housing said mold halves being pressed against each other at mutually facing mold parting surfaces thereof by a pressure-exerter in order to make the mold halves seal tightly against one another;

the mutually facing mold parting surfaces having mold cavities therein arranged in at least one row for receiving in each cavity said wire or thread for joining small molded bodies to one another to form the string of beads;

the mold cavities being respectively connected to a gate opening at a mold outer surface; and the plurality of mold cavities of a row being connected to a common runner formed in an inner wall of the mold housing through which an injection opening is formed for connection in a sealed manner to an injection device;

the injection device including therein a mixture of the bone cement and the at least one pharmaceutically active substance for injection into the mold cavities to form the small molded bodies which are joined to one.

2. An arrangement according to claim 1, wherein the gates of the mold cavities are arranged in the region of the mold parting surface and at points of least possible distance between the mold cavity and the mold outer surface.

3. An arrangement according to claim 1, wherein the two mold halves have two parallel rows of mold cavities, the gates of which open out in opposing mold outer surfaces, and wherein the runners and the injection openings are arranged in mutually opposing walls of the mold housing.

4. An arrangement according to claim 1, wherein the mold housing comprises a cross-sectionally U-shaped basic housing part and a removably fastened housing cover.

5. An arrangement according to claim 1, wherein the pressure-exerter comprises a plurality of countersunk screw connections, perpendicular with respect to the mold parting surface of the mold halves, in the mold halves themselves.

6. An arrangement according to claim 1, wherein at least two bolt pins are in one mold half, extending perpendicular to the mold parting surface, and corresponding depressions for receiving the pins are on the other mold half to position the mold halves.

7. A kit for making strings of treatment beads comprising:

a quantity of bone cement;

a pharmaceutically active substance;

a strand; and an apparatus for molding implants containing pharmaceutically active substances within the bone cement said apparatus comprising:

first and second mold halves each having at least two parallel rows of substantially semi-spherical recesses therein which when opposed form substantially spherical chambers, each substantially spherical chamber having an outer wall portion adjacent to outer walls of the mold halves and interior wall portions disposed generally normal to the outer wall portions;

first passages through the outer walls of the mold halves and the outer wall portions of the substantially spherical chambers;

second passages through the interior wall portions of the substantially spherical chambers and in the mold halves for connecting adjacent substantially spherical chambers in series;

an arrangement for holding the first and second mold halves in abutment with the substantially semispherical recesses aligned so as to form the substantially spherical chambers;

two outer bodies, each body being disposed outside of the outer walls of the mold halves when the mold halves are in abutment, the body having a space in communication with the first passages wherein said strand is placed in the second passages to extend through the substantially spherical chambers and wherein a mixture of the bone cement and the pharmaceutically active substance are dispensed from the space in the body through the first passages and into the substantially spherical chambers to form the string of treatment beads.

* * * * *